United States Patent [19]

Jacquet et al.

[11] 4,376,114

[45] Mar. 8, 1983

[54] COPOLYMERS OF N-VINYL PYRROLIDONE AND A VINYLIC, ALLYLIC OR METHALLYLIC ESTER OF A CYCLIC α- OR β- CARBOXYLIC ACID; AND COSMETIC COMPOSITIONS CONTAINING THE SAME

[75] Inventors: Bernard Jacquet, Antony; Christos Papantoniou, Montmorency; Guy Vanlerberghe, Montjay La Tour; Jean Mondet, Sevran, all of France

[73] Assignee: Societe Anonyme dite: L'Oreal, Paris, France

[21] Appl. No.: 313,488

[22] Filed: Oct. 21, 1981

Related U.S. Application Data

[62] Division of Ser. No. 118,634, Feb. 4, 1980, Pat. No. 4,321,348.

[30] Foreign Application Priority Data

Feb. 8, 1979 [FR] France .............................. 79 03261

[51] Int. Cl.$^3$ ............................................... A61K 7/11

[52] U.S. Cl. ................................ 424/47; 424/DIG. 1; 424/DIG. 2; 424/70

[58] Field of Search .................... 526/218; 424/47, 70

[56] References Cited

U.S. PATENT DOCUMENTS

| | | | |
|---|---|---|---|
| 2,578,950 | 12/1951 | Scheibli et al. | 526/326 |
| 3,164,573 | 1/1965 | Schweiker | 526/282 |
| 3,518,241 | 6/1970 | Duling et al. | 526/282 |
| 3,533,947 | 10/1970 | Duling et al. | 526/282 |
| 3,639,362 | 2/1972 | Duling et al. | 526/282 |
| 3,816,565 | 6/1974 | Takahashi | 526/264 |
| 3,899,461 | 8/1975 | Barabas et al. | 526/264 |
| 4,282,203 | 8/1981 | Jacquet et al. | 424/DIG. 1 |

*Primary Examiner*—Dale R. Ore
*Attorney, Agent, or Firm*—Cushman, Darby & Cushman

[57] ABSTRACT

The copolymer of N-vinyl pyrrolidone and a vinylic, allylic or methallylic ester of a cyclic α- or β- carboxylic acid is employed as a cosmetic film forming resin in cosmetic compositions for the hair, including hair setting lotions and lacquers, hair rinses and shampoos.

11 Claims, No Drawings

COPOLYMERS OF N-VINYL PYRROLIDONE AND A VINYLIC, ALLYLIC OR METHALLYLIC ESTER OF A CYCLIC α- OR β- CARBOXYLIC ACID; AND COSMETIC COMPOSITIONS CONTAINING THE SAME

This is a division of application Ser. No. 118,634 filed Feb. 4, 1980, now U.S. Pat. No. 4,321,348.

The present invention relates to copolymers of N-vinylpyrrolidone and a vinylic, allylic or methallic ester of a cyclic α- or β-carboxylic acid, these copolymers being useful in cosmetic compositions, and, principally, in cosmetic compositions for treating the hair, including hair setting lacquers and lotions.

Polyvinylpyrrolidone (PVP) forms on the hair a film which is both elastic and strong and has been largely utilized in cosmetic formulations such as hair setting lacquers and lotions.

However, the use of polyvinylpyrrolidone has been shown to be totally satisfactory only when the atmospheric humidity is relatively low. In effect, polyvinylpyrrolidone exhibits a certain hygroscopicity so that after a certain period of time in a humid atmosphere, the polyvinylpyrrolidone film tends to become sticky. In an effort to alleviate observed disadvantages due to the hygoscopicity of polyvinylpyrrolidone, it has been proposed to use copolymers of N-vinylpyrrolidone and vinyl acetate. Such copolymers are less sensitive to atmospheric humidity. Further, they exhibit good hair fixing or holding characteristics. By varying the proportion of vinyl acetate in such copolymers, it is possible to adjust certain properties of the film, principally its durability and hygroscopicity characteristics.

However, these N-vinylpyrrolidone/vinyl acetate copolymers do not always exhibit a very good lacquering power and films resulting therefrom can be relatively brittle.

The present invention provides a remedy for disadvantages of films produced from N-vinylpyrrolidone by providing new copolymers obtained by the polymerization of N-vinylpyrrolidone and at least one vinylic, allylic or methallylic ester of a cyclic α- or β-carboxylic acid.

In effect, it has now been noted by the applicants that by polymerizing N-vinylpyrrolidone with the above type of ester, the resulting copolymers exhibit excellent cosmetic properties. That is, the film resulting therefrom exhibits average durability, very low hygroscopicity, good lacquering power and an agreeable feel or touch.

The present invention thus relates to a copolymer having units releasing from the polymerization of:
(a) N-vinylpyrrolidone, and
(b) at least one vinylic, allylic or methallylic ester of acryclic α- or β-carboxylic acid having the formula:

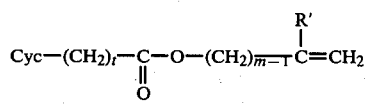  (I)

wherein:
R' represents hydrogen or methyl,
m is 1 or 2,
t is 1 or 2, when t=1, Cyc represents a mono- or poly-cyclic radical, saturated or unsaturated, such as:
(i) a radical of the formula,

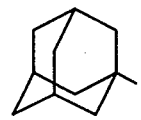

(ii) a radical of the formula,

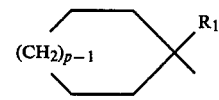

wherein $R_1$ represents hydrogen or methyl and p is 1 or 2,
(iii) a radical of the formula,

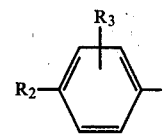

wherein $R_2$ represents hydrogen, methyl, ethyl, tert. butyl, ethoxy, butoxy or dodecoxy, and $R_3$ represents hydrogen, alkyl having 1-4 carbon atoms, or alkoxy having 1-4 carbon atoms, or
(iv) a radical of the formula,

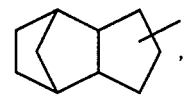

and when t=2, Cyc represents a radical of the formula,

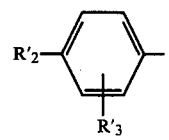

wherein $R'_2$ and $R'_3$ have the same meanings given for $R_2$ and $R_3$, above, respectively.

Representative vinylic, allylic or methallylic esters of formula (I) include, for instance, the vinylic, allylic or methallylic esters of 1-adamantane carboxylic acid, cyclohexane carboxylic acid, cyclopentane carboxylic acid, benzoic acid, phenylacetic acid, 4-tert. butyl benzoic acid, 1-methyl cyclopentane 1-carboxylic acid, 1-methyl cyclohexane 1-carboxylic acid, tricyclo-[5.2.1.0.$^{2,6}$] decane 3-carboxylic acid and tricyclo-[5.2.1.0.$^{2,6}$] decane 4-carboxylic acid. These latter two acids are sold, in the form of a mixture, under the tradename "TCD Carboxylic Acid S".

In accordance with another embodiment of the present invention, the copolymers can also contain units of at least one other monomer selected from:
1. a vinylic, allylic or methallylic ester of the formula,

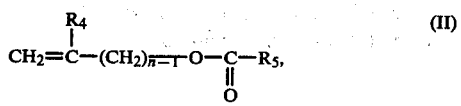

wherein n is 1 or 2, $R_4$ represents hydrogen or methyl, and $R_5$ represents linear or branched alkyl having 1-21 carbon atoms. Representative esters of formula II include the vinylic, allylic and methallylic esters of acetic acid, propionic acid, butyric acid, pivalic acid, hexanoic acid, octanoic acid, decanoic acid, lauric acid, myristic acid, palmitic acid, stearic acid, isostearic acid, behenic acid, 2-ethyl hexanoic acid, 2,2-dimethyl pentanoic acid, 2,2-dimethylhexanoic acid, 2,2-dimethyl octanoic acid, 2,2-dimethyl decanoic acid, 2,2,4,4-tetramethyl valeric acid, 2-isopropyl-2,3-dimethyl butyric acid, 2-methyl-2-ethyl heptanoic acid, 2-methyl-2-propyl hexanoic acid, 2-methyl-2-isopropyl hexanoic acid, 3,5,5-trimethyl hexanoic acid and isomers thereof, as well as mixtures of certain ones of these acids and principally a mixture sold under the tradename "d'Acide Versatique", and mixtures sold under the tradenames "d'Acides CEKANOIC $C_8$, $C_9$ and $C_{10}$";

2. a vinyl ether of the formula, $CH_2=CH-OR_6$ (III), wherein $R_6$ represents linear or branched alkyl having from 6 to 18 carbon atoms. Representative vinyl ethers of formula III include hexylvinyl ether, octylvinyl ether, decylvinyl ether, dodecylvinyl ether, hexadecylvinyl ether and octadecylvinyl ether; and 3. an α-olefin of the formula, $CH_2=CH-(CH_2)_s-CH_3$ (IV) wherein s is a whole number from 3-15. Representative α-olefins of formula IV include 1-hexene, 1-octene, 1-decene, 1-dodecene and 1-octadecene.

The copolymers of the present invention can be represented by the following formula:

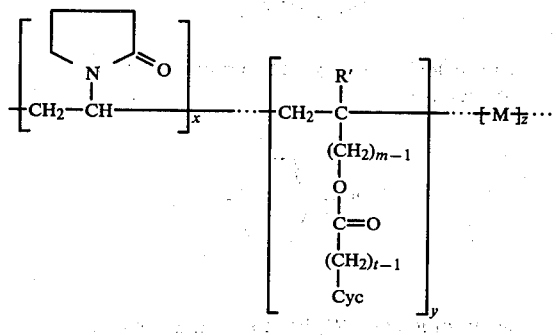

wherein:

Cyc, R', m and t have the same meanings given above,

M is a unit derived from at least one monomer such as represented by formulas (II) to (IV), above, x represents from 20 to 90 weight percent, and preferably from 25 to 80 weight percent, y represents from 1 to 70 weight percent, and preferably from 10 to 50 weight percent, and z represents from 0 to 70 weight percent, and preferably from 10 to 60 weight percent.

However, it is important to note that the sum of the non-homopolymerizable monomers in the copolymer of the present invention cannot exceed 50 molar percent of the total of the monomers used to produce the copolymer. The non-homopolymerizable monomers, in accordance with the invention, are:

(i) the compounds of formula I when m=2,
(ii) the compounds of formula II when n=2, and
(iii) the compounds of formulas III and IV.

In a preferred embodiment, when m=2 in the monomers of formula I, x, y and z have the following molar percentages: s represents from 50 to 90 percent; y represents from 10 to 50 percent and z represents from 0 to 40 percent.

The copolymers in accordance with the present invention, such as defined above, have an average molecular weight ranging between 5,000 and 60,000 and, more particularly, between 10,000 and 45,000. These molecular weights are average molecular weights, numerically determined by osmometry.

The present invention also relates to the process of preparing these copolymers.

They can be obtained by classic polymerization methods, that is, either in solution in a solvent, in mass, or even in suspension in an inert liquid or in emulsion.

In accordance with another embodiment of the present invention, the polymerization reaction is carried out in suspension in water saturated with sodium chloride and in the presence of a protective colloid or suspension agent such as, for example, polyvinyl alcohol, cross-linked polyacrylic acid, the product known commercially as Cellosize WP-09. This process provides, at the end of the reaction, the desired copolymer in pearl form.

The polymerization initiators which can be used in the polymerization process of this invention are, preferably: azobisisobutyronitrile, peresters, percarbonates or oxido-reduction systems. The polymerization initiator can be used either singly or as an admixture thereof.

The amount of the polymerization initiator is generally between 0.1 and 6 weight percent relative to the total weight of the monomers being copolymerized.

The polymerization reaction is preferably carried out at a temperature between 45° and 100° C. and, more particularly, at the reflux temperature of the reaction mixture.

The reaction time is preferably between 6 and 24 hours.

The present invention also relates to a cosmetic composition for treating the hair containing as the cosmetic film forming resin at least one copolymer of the present invention, as defined above, these compositions being provided in the form of hair setting lotions, aerosol lacquers, rinses or shampoos.

In accordance with the present invention, the cosmetic compositions contain from 0.5 to 10 weight percent of at least one copolymer defined above.

The hair setting lotions, in accordance with the present invention are provided in the form of an aqueous or hydroalcoholic solution, containing from 20 to 70 weight percent alcohol and having a copolymer concentration between, preferably, 1 and 3 weight percent.

The alcohols generally employed for the production of such hair setting lotions are, preferably, low molecular weight aliphatic alcohols, such as ethanol or isopropanol.

The aerosol hair lacquers, in accordance with the present invention, are obtained by solubilizing in an alcohol at least one copolymer as defined above, this solution then being packaged in an aerosol container, pressurized or not.

In accordance with this embodiment of the invention, the copolymer is preferably employed in an amount between 0.7 and 8 weight percent.

The aerosol hair lacquers can also contain a third or auxiliary solvent which can be present in an amount between 3 and 35 weight percent.

Representative third or auxiliary solvents include, for instance, methylene chloride, trichloroethane, ethyl chloride, acetone, ethyl acetate and dichlorodifluoroethane.

In the aerosol hair lacquers, according to the present invention, the alcohol whch can also be either ethanol, or isopropanol, is generally present in an amount between 5 and 80 weight percent and preferably between 6 and 70 weight percent.

Representative propellant agents for use in preparing the aerosol hair lacquers include, in particular, fluorinated hydrocarbons, either singly, or in admixture with other such fluorinated hydrocarbons, or principally, those known commercially as "Freons", and in particular Freons 11, 12, 22, 133A and 142B.

As the propellant agent, there can also be employed $CO_2$, $N_2O$, dimethylether, hydrocarbons such as propane, butane and isobutane. These propellant agents are used singly or as an admixture thereof or with one or more "Freons" such as listed above.

When the cosmetic composition of this invention is also provided in the form of a shampoo it contains, in addition to the copolymer of the invention, at least one anionic, cationic or non-ionic surfactant.

The cosmetic composition of the present invention can also contain various components generally used in this type of composition, such as plasticizers, hair shining agents, perfumes, dyes and hair restructuring agents.

In order to better understand the invention, the following non-limiting Examples of preparing the copolymers as well as several examples of cosmetic compositions in the form of hair setting lotions and aerosol hair lacquers are given. Unless otherwise specified all parts and percentages are by weight.

EXAMPLES OF COPOLYMER PREPARATION

Example 1

In a round bottom flask fitted with a condenser, a mechanical agitator and a nitrogen lead-in tube, there are introduced 35 g of vinyl 4-tert. butyl benzoate, 35 g of vinyl acetate, 30 g of N-vinyl pyrrolidone and 0.2 g of azobisisobutyronitrile in solution in 30 g of ethanol.

The mixture is then heated to reflux with agitation for 24 hours. The resulting copolymer is precipitated in ethyl ether. After filtration the said copolymer is dried at 50° C. under reduced pressure.

The copolymer yield is 42% and the copolymer obtained exhibits a viscosity of 1.56 centipoises, measured in a 5% solution in dimethylformamide (DMF) at 34.6° C.

Example 2

In a round bottom flask, fitted with a condenser, a mechanical agitator and a nitrogen lead-in tube, there are introduced 30 g of N-vinylpyrrolidone, 15 g of vinyl cyclohexanoate, 55 g of vinyl acetate, 0.5 g of tert. butyl 2-ethyl perhexanoate and 25 g of ethanol.

The mixture is then heated to reflux with agitation for 24 hours. After the end of the polymerization reaction, the resulting copolymer is precipitated in ethyl ether.

After filtration the copolymer is dried at 50° C. under reduced pressure.

The copolymer yield is 80% and the copolymer obtained exhibits a viscosity of 2.4 centipoises measured in a 5% solution of dimethylformamide (DMF) at 34.6° C.

Using the procedures described in Examples 1 and 2 above, the copolymers listed in Table I, below, have also been prepared.

TABLE I

| Monomers, weight % | Ex. 3 * | Ex. 4 * | Ex. 5 * | Ex. 6 * | Ex. 7 * | Ex. 8 * | Ex. 9 * | Ex. 10 * | Ex. 11 * | Ex. 12 * | Ex. 13 ** | Ex. 14 * |
|---|---|---|---|---|---|---|---|---|---|---|---|---|
| N—vinyl pyrrolidone | 70 | 50 | 30 | 70 | 50 | 40 | 30 | 35 | 40 | 40 | 30 | 35 |
| vinyl 4-tert butyl benzoate | 30 | 50 | 70 | 15 | 25 | | | | | | | |
| allyl 4-tert butyl benzoate | | | | | | 10 | | | | 5 | | |
| vinyl benzoate | | | | | | | 15 | | | | | 12 |
| vinyl cyclopentanoate | | | | | | | | 15 | 5 | | 15 | |
| vinyl phenylacetate | | | | | | | | | | 10 | | |
| allyl benzoate | | | | | | | | | 10 | | | |
| vinyl acetate | | | | 15 | 25 | 50 | 50 | 45 | | 40 | 50 | 38 |
| vinyl propionate | | | | | | | | | 45 | | | |
| allyl propionate | | | | | | | | | | 5 | | 10 |
| allyl stearate | | | | | | | 5 | | | | | 5 |
| octadecyl vinyl ether | | | | | | | | | | | 5 | |
| dodecyl vinyl ether | | | | | | | | 5 | | | | |
| yield % | 80 | 62 | 26 | 73.2 | 70 | 40 | 42 | 55 | 48 | 59 | 92 | 64 |
| Viscosity (5% solution in DMF at 34.6° C.), cps. | 2.05 | 1.89 | 1.67 | 1.88 | 1.54 | 1.52 | 1.82 | 1.69 | 1.54 | 1.68 | 2.3 | 1.73 |

*obtained in accordance with the process of Example 1
**obtained in accordance with the process of Example 2

EXAMPLES OF COSMETIC COMPOSITIONS

Example A

In accordance with the present invention an aerosol hair lacquer is prepared by packaging in an aerosol container the following components:

| | |
|---|---|
| Copolymer of Example 1 | 3g |
| Ethanol (or isopropanol) | 40g |
| Methylene chloride | 20g |
| Propellant: | |
| mixture of 35% propane/65% butane | 40g |

In this example the copolymer prepared in accordance with Example 1 can be replaced by the same amount of the copolymer prepared in accordance with Example 4.

Example B

In accordance with the present invention an aerosol hair lacquer is prepared by admixing the following components:

| | |
|---|---|
| Copolymer of Example 3 | 3g |
| Ethanol | 60g |
| Propellant: | |
| mixture of 35% propane/65% butane | 40g |

Example C

In accordance with the present invention an aerosol hair lacquer is prepared by admixing the following components:

| | |
|---|---|
| Polymer of Example 2 | 7.6g |
| Ethanol, sufficient for | 100g |

22 g of the composition thus obtained are then packaged in an aerosol container, together with 78 g of a mixture of Freon 11/Freon 12 (61.5%/38.5%).

When this hair lacquer is applied to the hair no powdering over a prolonged period of time is observed. Further the hair does not become sticky even in a humid atmosphere.

Example D

In accordance with the present invention a hair setting lotion is prepared by admixing the following components:

| | |
|---|---|
| Polymer of Example 4 | 2g |
| Perfume | 0.15g |
| Ethanol | 46g |
| Water, sufficient for | 100g |

In this Example, the polymer prepared in accordance with Example 4 can advantageously be replaced by the same amount of one of the polymers prepared in accordance with Examples 5 to 8 or 14.

After applying this hair setting lotion to the hair, the hair is rolled up on hair setting rollers, and then dried. The resulting hair set has a very good hold over a prolonged period time and no powdering of the resin film is observed.

Example E

In accordance with the present invention a hair setting lotion is prepared by admixing the following components:

| | |
|---|---|
| Polymer of Example 9 | 3.5g |
| Perfume | 0.2g |
| Dye, sufficient to color the hair setting lotion | 0.15g |
| Isopropyl alcohol | 50g |
| Water, sufficient for | 100g |

This hair setting lotion, applied in a conventional manner, to the hair imparts thereto a shiny appearance and an excellent long-lasting hold.

In this Example, the polymer prepared in accordance with Example 9 can advantageously be replaced by the same amount of one of the polymers prepared according to Examples 10 to 12.

Example F

In accordance with the present invention a hair rinsing product, or "hair rinse" is prepared in the form of an emulsion by admixing the following components:

| | |
|---|---|
| Petrolatum oil | 9.6g |
| Fatty alcohol (C$_{16-18}$) polyglycerolated with 2-6 moles of glycerol | 6.5g |
| Polymer of Example 13 | 1.5g |
| Water, sufficient for | 100g |

This product is applied to washed and dried hair by carefully distributing it throughout all the hair. After a contact period of a few minutes, the hair is carefully rinsed. The hair thus treated is shiny and easy to comb.

In this Example the polymer of Example 13 can advantageously be replaced by the same amount of one of the polymers prepared according to Examples 2 to 5 and 8.

Example G

In accordance with the present invention an anionic shampoo is prepared by admixing the following components:

| | |
|---|---|
| Triethanolamine lauryl myristyl sulfate | 12g |
| Copra diethanolamide | 2g |
| Dimethylamine myristyl oxide | 1.5g |
| Polymer of Example 10 | 1.5g |
| Lactic acid, sufficient for pH = 6.5 | |
| Water, sufficient for | 100g |

Example H

In accordance with the present invention a cationic shampoo is prepared by admixing the following components:

| | |
|---|---|
| Lauryl alcohol polyglycerolated with 4 moles of glycerol | 12g |
| Cetyl trimethylammonium bromide | 2g |
| Polymer of Example 6 | 1g |
| Perfume | 0.2g |
| Lactic acid, sufficient for pH = 4.5 | |
| Water, sufficient for | 100g |

In this Example, the polymer prepared in accordance with Example 6 can advantageously be replaced by the same amount of one of the polymers prepared according to Examples 7 or 13.

What is claimed is:

1. A cosmetic composition in the form of hair setting lotions, aerosol lacquers, rinses or shampoos for treating the hair comprising in a cosmetic vehicle an effective amount of at least one copolymer consisting of units of the formula

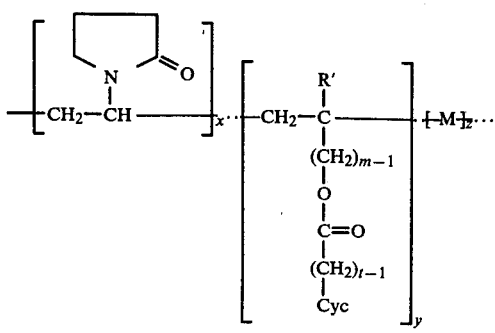

wherein
R' represents hydrogen or methyl,
m is 1 or 2
t is 1 or 2,
when t=1, Cyc represents
(i) a radical of the formula

(ii) a radical of the formula

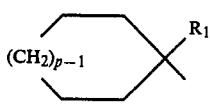

wherein $R_1$ represents hydrogen or methyl, and p is 1 or 2,
(iii) a radical of the formula

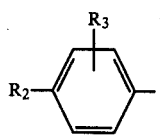

wherein $R_2$ represents hydrogen, methyl, ethyl, tert. butyl, ethoxy, butoxy or dodecoxy, and $R_3$ represents hydrogen, alkyl having 1–4 carbon atoms or alkoxy having 1–4 carbon atoms, or
(iv) a radical of the formula

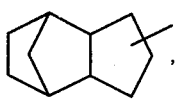

and when t=2, Cyc represents a radical of the formula

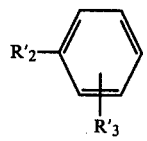

wherein $R'_2$ and $R'_3$ have the same meanings as those for $R_2$ and $R_3$, respectively,
M is a unit derived from a monomer selected from the group consisting of
(i') a monomer having the formula

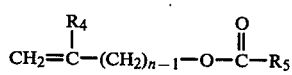

wherein n is 1 or 2, $R_4$ represents hydrogen or methyl and $R_5$ represents linear or branched alkyl having 1–21 carbon atoms,
(ii') a monomer having the formula $CH_2=CH-OR_6$ wherein $R_6$ is linear or branched alkyl having 6–18 carbon atoms, and
(iii') a monomer having the formula $CH_2=CH-(CH_2)_s-CH_3$, wherein s is a whole number from 3 to 15,
x represents from 20 to 90 weight percent,
y represents from 10 to 80 weight percent, and
z represents from 0 to 70 weight percent, with the proviso that the total sum of non-homopolymerizable monomers does not exceed 50 mole percent of the total monomers in said copolymer.

2. The cosmetic composition of claim 1 wherein x represents 25–80 weight percent, y represents 10–50 weight percent and z represents 10–60 weight percent.

3. The cosmetic composition of claim 1 wherein said copolymer has an average molecular weight, determined by osometry, ranging from 5,000 to 60,000.

4. The cosmetic composition of claim 1 wherein said copolymer has an average molecular weight, determined by osometry, ranging from 10,000 to 45,000.

5. The cosmetic composition of claim 1 wherein said copolymer is present in an amount between 0.5 to 10 weight percent thereof.

6. The cosmetic composition of claim 1 wherein said cosmetic vehicle is water or a hydroalcoholic solution and said copolymer is present in an amount from 1 to 3 percent by weight of said composition.

7. The cosmetic composition of claim 1 wherein said cosmetic vehicle is an alcohol in admixture with a propellant agent, said composition being packaged in an aerosol container and wherein said copolymer is present in an amount between 0.7 and 8 percent by weight of said composition.

8. The cosmetic composition of claim 6 wherein the alcohol of said hydroalcoholic solution is ethanol or isopropanol.

9. The cosmetic composition of claim 7 wherein said alcohol is ethanol or isopropanol.

10. The cosmetic composition of claim 7 which includes an auxiliary solvent present in an amount between 3 and 35 weight percent relative to the total weight of said composition.

11. The cosmetic composition of claim 1 which also contains an effective amount of an anionic, cationic or non-ionic surfactant.

* * * * *